United States Patent [19]

Sheridan et al.

[11] Patent Number: 4,883,474
[45] Date of Patent: Nov. 28, 1989

[54] THORACIC CATHETER

[75] Inventors: David S. Sheridan, Hook Rd., Argyle, N.Y. 12809; Ralph D. Alley, Loudonville, N.Y.

[73] Assignee: David S. Sheridan, Argyle, N.Y.

[21] Appl. No.: 62,844

[22] Filed: Jun. 16, 1987

Related U.S. Application Data

[63] Continuation-in-part of Ser. No. 891,919, Jul. 30, 1986, abandoned, which is a continuation-in-part of Ser. No. 885,477, Jul. 14, 1986, abandoned.

[51] Int. Cl.[4] ............................................. A61M 5/00
[52] U.S. Cl. .................................... 604/280; 128/339; 604/272
[58] Field of Search .............. 604/164, 165, 170, 264, 604/272, 273, 274, 280, 281, 282; 128/339

[56] References Cited

U.S. PATENT DOCUMENTS

| Re. 25,788 | 6/1965 | Sheridan | 604/283 |
|---|---|---|---|
| 1,529,238 | 3/1925 | Broz | 604/164 |
| 2,857,915 | 10/1958 | Sheridan . | |
| 3,042,044 | 7/1962 | Sheridan | 604/283 |
| 3,094,124 | 6/1963 | Birtwell | 604/280 |
| 3,190,290 | 6/1965 | Alley et al. . | |
| 3,295,527 | 1/1967 | Alley et al. | 604/280 |
| 3,459,189 | 8/1969 | Alley et al. . | |
| 3,528,427 | 9/1970 | Sheridan . | |
| 3,584,624 | 6/1971 | de Ciutiis | 604/272 |
| 3,788,328 | 1/1974 | Alley et al. . | |
| 3,903,895 | 9/1975 | Alley et al. . | |
| 4,359,053 | 11/1982 | Benjamin | 128/339 |
| 4,431,426 | 2/1984 | Groshong et al. | 604/164 |
| 4,432,752 | 2/1984 | Marlon | 604/164 |
| 4,453,928 | 6/1984 | Steiger | 604/164 |
| 4,490,136 | 12/1984 | Ekbladh et al. | 604/272 |
| 4,504,269 | 3/1985 | Durand | 604/272 |

Primary Examiner—Stephen C. Pellegrino
Assistant Examiner—Ralph Lewis
Attorney, Agent, or Firm—Wood, Dalton, Phillips, Mason & Rowe

[57] ABSTRACT

A thoracic catheter is provided with a distal end and a proximal end. The catheter is formed by a tube of flexible material having at least one radial opening at the distal end for draining a body cavity. The proximal end of the tube has a stiffened and sharpened portion whereby pressure applied to the stiffened proximal end from inside the body cavity leads the catheter outwardly through body tissue whereupon the sharpened stiffened proximal end can be severed and the catheter left in situ. The stiffened end is a rigid rod that extends outward of the proximal end of the tube and terminates in the tube short of a cut-off point whereby the tube is severed and the rod and severed proximal end portion is disposed of. The rigid rod may extend a substantial distance inside the tube and be shapable into a grippable shape to assist the user in maneuvering the rod and tube into and through a desired path in the surgical site.

28 Claims, 2 Drawing Sheets

THORACIC CATHETER

RELATED APPLICATION

This application is a Continuation-In-Part of Ser. No. 891,919 filed on July 30, 1986 which in turn was a Continuation-In-Part of Ser. No. 885,477 filed on July 14, 1986.

FIELD OF THE INVENTION

This invention relates to a thoracic catheter and, more particularly, to a MARLIN Tip thoracic catheter wherein the trocar is formed integral with the catheter.

BACKGROUND OF THE INVENTION

Intercostal catheters are used for draining fluids, either gas or liquid, from the thoracic cavity in the operating arena following intrathoracic surgical procedures for post operative drainage, in the emergency room and in various other ambulatory or health care facilities.

In most surgical procedures wherein an original incision is made, such as in the chest cavity, catheters predominantly have been inserted through an outside body opening from the inside-out. The catheter is provided with a distal end and a proximal end. The catheter is inserted through the original incision with the proximal end portion entering the incision first. A second incision or body opening is made, and a forceps is inserted through the second incision outside-in to grasp the proximal end of the catheter. The catheter thereby is pulled through the second incision until the distal end portion is properly positioned with the tube leading out through the second incision. Then the proximal end is connected to an appropriate tubular connector leading to a source of negative pressure to apply suction for draining the body cavity. Such procedures often cause ripping, tearing and coring of body tissues because of the projecting barbs formed by the forceps or the catheter or both. Our U.S. Pat. No. 3,295,527, dated Jan. 3, 1967, discloses a vastly improved intercostal catheter which not only eliminates tearing and ripping of tissue as the proximal end is drawn through a second incision by forceps, but additionally eliminates any coring effect of the tissue created by the proximal end opening of the catheter. However, with the improved catheter of the aforesaid patent, an auxiliary implement such as the forceps, must be used for positioning the catheter in an outside-in procedure.

In order to eliminate the use of forceps or like instruments, a solution was disclosed in our U.S. Pat. No. 3,459,189, dated Aug. 5, 1969, which shows a novel intercostal catheter kit including a catheter with a mating, cooperating trocar. The trocar is provided with an abutment formed near its distal end for engaging an abutment internally of the catheter tube to force the catheter through a body opening or incision by means of the trocar itself. However, here again the trocar is a separate instrument and the kit or assembly normally must be used by piercing from the outside-in.

The use of intercostal catheters often becomes a further complicated and delicate procedure when operating on patients, such as small children or infants, having very small chest cavities. It can be seen from the above that, heretofore, placing a catheter in an inside-out procedure would have been practically unheard of because a surgeon actually must operate "in the blind", using the delicate feel of his fingers for sensing placement location. The present invention now makes that possible.

The present invention is directed to providing a new and improved thoracic trocar catheter comprised of a unitary structure which completely eliminates the need for using a separate forceps or separate trocar and in which the catheter itself can be used for piercing body tissue from a body cavity in an inside-out direction.

SUMMARY OF THE INVENTION

An object, therefore, of the invention is to provide a new and improved, unitary MARLIN Tip thoracic catheter.

MARLIN TIP is a trademark of Sheridan Catheter Corp. of Argyle, New York 12809.

In the exemplary embodiments of the invention, a MARLIN Tip thoracic catheter generally has a distal end and a proximal end and comprises a tube of flexible material having at least one radial opening at the distal end portion thereof for draining a body cavity. Sharpened stiffening means are provided at the proximal end portion of the flexible tube. Pressure can be applied to the stiffened proximal end portion from inside the body cavity to lead the catheter outwardly through body tissue whereupon the sharpened stiffening means can be severed and the catheter left in situ.

In one embodiment of the invention, the stiffening means comprises a rigid, preferably solid, rod disposed within and fixed to the inside of the tube at the proximal end portion thereof. The rigid rod includes a sharpened or chiseled distal end projecting from the proximal end of the tube. The tube may include a fusiform or enlarged portion axially inwardly of the proximal end and tapering toward an opening at the proximal end, the rigid rod being fixed to the tube within the opening. The tube may be of substantially uniform diameter with the rigid rod being fixed to the tube within the opening.

In another embodiment of the invention, the stiffening means comprises an integral portion of the tube itself. Specifically, a given length of the material of the tube at the proximal end thereof is shaped and hardened to form the stiffening means. The shaped and hardened proximal end of the tube terminates at an angle to sharpen the stiffened tube. The tube may include a tapered fusiform or enlarged portion axially inwardly of the proximal end thereof, with the hardened length of the tube extending only partially into the enlarged portion. The tube may be a substantially uniform diameter with the shaped and hardened length of the tube extending only partially into and joining with the uniform diameter portion of the tube.

In order to facilitate manipulating the rigid rod of the trocar catheter more accurately, it has been found that the rigid rod may be elongated axially outward of the proximal end of the tube and/or inside the proximal end of the tube. The material of the rigid rod can be shaped so as to act as a handle for manipulating the rigid rod around the exposed organs in the chest cavity to the site ready for penetration inside-out of the cavity. The elongated rigid rod makes it possible to place the tube in difficult places particularly in small chest cavities, such as a child's chest, or in an abnormal chest.

In one modified version, the portion of the rigid rod in the tube is terminated short of the maximum bulge in the enlarged section of the tube so that the tube, when in place, can be cropped to expose the funnel-shaped opening for a connector without running the risk of severing the rigid rod, thereby creating a loose fragment of said rigid rod, which could be lost within the operative site.

Other objects, features and advantages of the invention will be apparent from the following detailed description taken in connection with the accompanying drawings.

BRIEF DESCRIPTION OF THE DRAWINGS

The features of this invention which are believed to be novel are set forth with particularity in the appended claims. The invention, together with its objects and the advantages thereof, may be best understood by reference to the following description taken in conjunction with the accompanying drawings, in which like reference numerals identify like elements in the figures and in which:

DETAILED DESCRIPTION OF THE PREFERRED EMBODIMENTS

The present invention, in addition to providing a MARLIN Tip Thoracic Catheter available at all times for immediate use, provides a significant improvement over the tedious manipulative procedures that were required using forceps placement of a catheter for post-operative drainage. The invention completely eliminates the need for a separate incision large enough to accommodate a catheter grasping forceps whose jaws must be opened within a body cavity (i.e. thoracic cavity) in order to grasp a catheter and pull it through the chest wall for proper placement. This traditional catheter placement is referenced as the "outside-in method", following the path traversed by the catheter grasping forceps. The MARLIN Tip Catheter placement is referenced as the "inside-out method", following the path traversed by the penetrating spike, all of which will become apparent from the following description.

Figure 1:
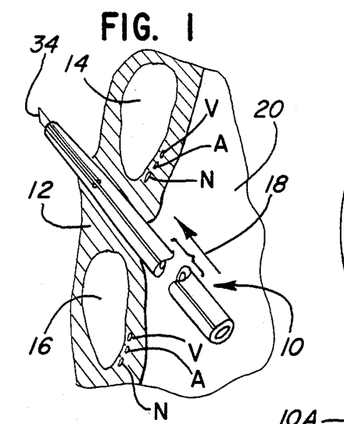
FIG. 1 is a view of a MARLIN Tip thoracic catheter placed through the thoracic wall of a patient.

More particularly, referring to the drawings in greater detail and first to FIG. 1, a MARLIN Tip thoracic catheter of this invention, generally designated 10, is inserted through body tissue 12, such as through a thoracic wall between ribs 14 and 16 (intercostal space), in an inside-out direction, as indicated by arrow 18, i.e. from inside a body cavity 20. As is shown in FIG. 1, a vein "V", an artery "A", and a nerve "N" called a neurovascular bundle is located in a neurovascular space located on the chest cavity side of each rib 14,16 at the narrow inferior edge of the rib. It will be seen from the structures of the embodiments of the invention disclosed herein, that manipulation of the catheter in an inside-out direction provides for greater certainty that the neurovascular bundle is avoided during catheter placement.

If the anatomy of the chest wall at the site selected for catheter insertion is normal, injury to the neurovascular bundle can be avoided by inserting the trocar at or near the upper border, thick side, of the rib lying below the intercostal space selected. If the anatomy of the chest is abnormal, whether due to congenital developmental abnormalities of the blood vessels supplying blood to the chest walls, or if the vascularity of the chest wall is increased by acquired inflammatory or neoplastic disease, the risk of hemorrhage resulting from catheter placement can be minimized by selecting the most favorable site under direct vision and palpation. The superiority of this method in reducing the risk of hemorrhage into the chest cavity is obvious. For, the catheter traverses a direction away from vital structures, as it moves through the various muscle layers encasing the chest wall.

Heretofore, the usual plan of catheter placement, employing a forceps or trocar inserted from the outside starts with the identification of an entry point which will insure that the tract followed by the catheter will pass through the structures of the chest wall, and in many instances upper abdominal muscular layers, so that the catheter emerges into the chest wall cavity at a site remote from the entry point at an angle of inclination that insures the catheter will follow the curvature of the internal aspect of the rib cage. By this means the portion of the catheter within the chest does not compress the underlying lung tissue or the heart. In order to do this safely requires the exercise of powers of depth perception and a clear conception of not only normal anatomy but abnormal anatomy of the subject case affecting structures and organs that might be at risk as the forceps or trocar are introduced and advanced.

Figure 2:
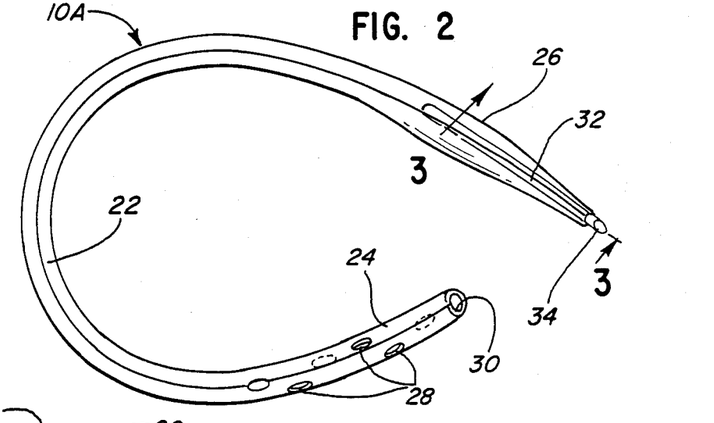
FIG. 2 is a perspective view of one embodiment of the invention.
Figures 3, 4, 5, 6, 7, 8:
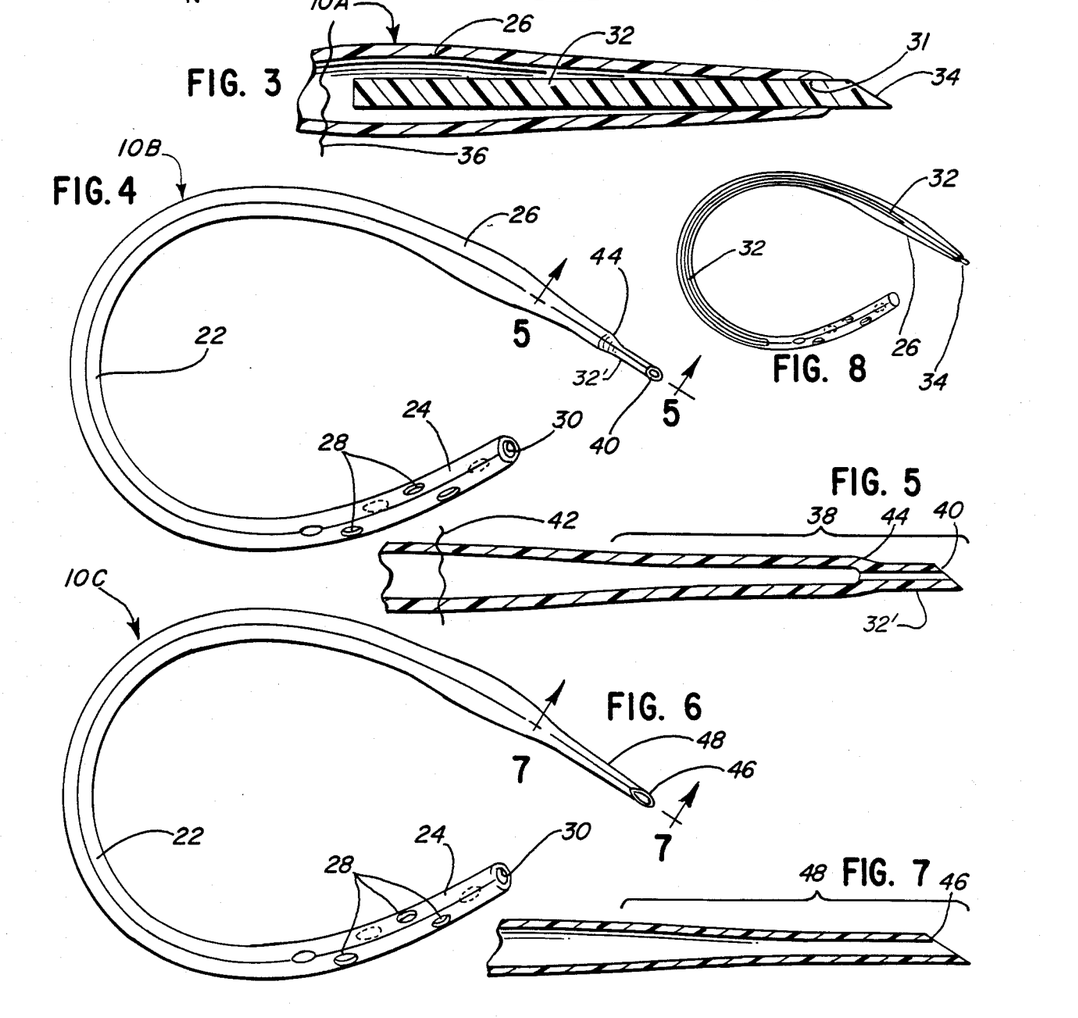
FIG. 3 is a fragmented axial section, on an enlarged scale, taken generally along line 3—3 of FIG. 2.
FIG. 4 is a perspective view similar to that of FIG. 2, illustrating another embodiment of the invention.
FIG. 5 is a fragmented axial section, on an enlarged scale, taken generally along line 5—5 of FIG. 4.
FIG. 6 is a perspective view of still another embodiment of the invention.
FIG. 7 is a fragmented axial section, on an enlarged scale, taken generally along line 7—7 of FIG. 6.
FIG. 8 is a modified form of the invention showing the trocar extended both inside and outside the catheter.

FIGS. 2 and 3 illustrate one embodiment of the invention in the form of a unitary MARLIN Tip catheter, generally designated 10A. The catheter is flexible and includes a tube portion 22, a distal end portion 24 and a fusiform proximal end portion 26. The distal end portion has a series of radial inlet openings 28 and an open distal end 30. The proximal end portion 26 is enlarged with a gradual flare to form a bulbous configuration which may be severed at an appropriate location to form a connector as described hereinafter. When severed, the flared proximal end may fit with an appropriate mating connector of varying diameter leading to a source of negative pressure for applying suction to the catheter to withdraw fluids from the body cavity. The catheter may be constructed of a seamless, flexible plastic material which is transparent to both light and X-rays although some catheters may have an X-ray opaque line as shown in Sheridan U.S. Pat. No. 2,857,915. The plastic material is particularly flexuous at body temperatures but is not unduly soft for its function as a catheter. For instance, at body temperature, the tube becomes sufficiently flexuous, as by hand working (i.e. pulling on the catheter tube with a warm hand as the warm hand is drawn or slid along the tube many times) that the catheter can be shaped into the most advantageous configuration for ease in manipulating the catheter in the chest cavity and for locating the trocar end for puncturing an intercostal space in a thoracic wall in an inside-out direction. The catheter may be made of any material that is flexible such as rubber or the like.

Generally, the invention contemplates providing sharpened stiffening means unitary with and at the proximal end portion of the catheter whereby pressure can be applied to the stiffened proximal end portion from inside the body cavity to penetrate the stiffened proximal end outwardly through the body tissue as will be described hereinafter. The catheter is then worked through the body wall until the distal end is in position whereupon a segment of the bulbous portion is severed to remove the sharpened stiffening means with the catheter left in situ for its intended use.

In the embodiment of the invention shown in FIGS. 2 and 3, the stiffening means for the MARLIN Tip thoracic catheter 10A comprises a rigid rod 32 disposed within and fixed to the inside of an open end 31 at the proximal end 26 of the tube. The rod may be fabricated of plastic material or other material, such as metal, wood, bone, ivory or the like as long as it is considerably more rigid than the material of tube 22. The rod is fixed to the tube within opening 31 so as to be unitary or integral therewith, as by heat, ultrasonic welding or other welding methods, or by the use of a solvent or cement at the interface between the tube and rod. The rod is sharpened or chiseled, as at 34, at the outer end thereof projecting from the proximal end of the catheter for piercing body tissue. In the illustrated embodiments of FIGS. 2 and 3 the rod extends only a short distance outward of the tube. It is contemplated that the rod could extend outward of the tube an extra distance for specific purposes and procedures.

The stiffening means or rod 32 may be of a plastic material having the same characteristic of becoming somewhat flexuous at body temperature as does the plastic material of the tube 22 of the catheter 10. For instance, by hand working the tube 22 and rod 32 the rod can be formed into an appropriate shape such as a J shape or the like.

In some cases such as shown in FIG. 8 the stiffening means or rod may be plastic or metal, bone, wood, ivory or the like and may extend all the way or almost all the way through the length of the tube 22 for use in special circumstances. For instance, with a patient having either a condition where the exposed organs in the chest cavity cannot take the pressure caused by a surgeon's hand being inserted into the chest cavity with the catheter rod end poised for penetration inside-out of the cavity or where the chest cavity is too confined to receive the surgeon's hand, an elongate clamp is applied to the rod end of the catheter for remote positioning in the proper place in the chest cavity and then by grasping the remote end of the stiffening means or rod and catheter the trocar end can be forced inside-out through the chest wall.

In operation, during surgery after the catheter is inserted and pierced through the body wall tissue as described above, tube 22 is cut or severed, as at 36, to simultaneously remove rod 32 and to form a connector. The catheter is left in situ ready for draining fluids from the body cavity.

FIGS. 4 and 5 show a second embodiment of the invention wherein the stiffening means for a catheter, generally designated 10B, comprises an integral portion of tube 22. Like numerals are applied to the embodiment of FIGS. 4-5 corresponding to like elements in the embodiment of FIGS. 2-3. More particularly, the tube 22 is of a plastic material and has a given length, such as that indicated at 38, which is hardened to form integral stiffening means for the catheter. In other words, length 38 does not comprise a flexuous portion of the catheter. The given length 38 includes a rod-like portion 32' integrally formed with the tube 26 by a shoulder 44. Since length 38 is made stiff by hardening, the catheter can pierce the body tissue of a patient. The extreme distal end of hardened length 38 is formed at an angle, as at 40, to sharpen the hardened, stiffened rod-like end 32' of the catheter. It can be seen that hardened length 38 extends only partially into the enlarged bulbous portion 26 of the catheter whereby the hardened length can be severed, as at 42, to leave the remainder of the enlarged end flexuous for accommodating connecting means to the source of negative pressure. If the catheter is of substantially uniform diameter, the integral stiffening means can be severed after placement of the catheter whereupon an appropriate suction device is attached for drainage of the site.

The tubing when made of plastic material, such as polyvinylchloride, is selectively hardened by a leeching process which involves dipping the tubing in a solution such as alcohol. The plastic material of the tubing originally is made flexuous by a plasticizer component. Leeching draws out the plasticizer and leaves the tubing hard or stiffened. The degree of hardness depends on the time and temperature parameters of soaking the tubing in the alcohol.

FIGS. 6 and 7 show a further embodiment of the invention wherein shoulder 44 (FIG. 5) has been eliminated and the proximal fusiform end of a catheter 10C is provided with a general taper to a sharpened end 46 thereof. As with the embodiment of FIGS. 4-5, a given length 48 of the plastic material of the catheter tubing is hardened at the proximal end of the catheter, as by leeching, to form stiffening means to pierce the body tissue. The leeching process also tends to slightly shrink the tubing since the plastic material is being reduced by removing the plasticizer component.

In essence, the stiffening means or rod 32 in the embodiment of FIGS. 2, 3 and 8 or the hardened tubing in the embodiments of FIGS. 4-7, acts as a handle for the surgeon to manipulate the MARLIN Tip catheter and pierce the body tissue. As can be readily seen in FIG. 8, the rod 32 runs substantially the greater portion of the length of the catheter so that both the catheter and handle can be grasped simultaneously. By being able to insert the catheter from the inside-out, it is much easier and more certain to avoid piercing the neurovascular bundle of a patient, even small patients with very small chest cavities.

Figures 9, 10:
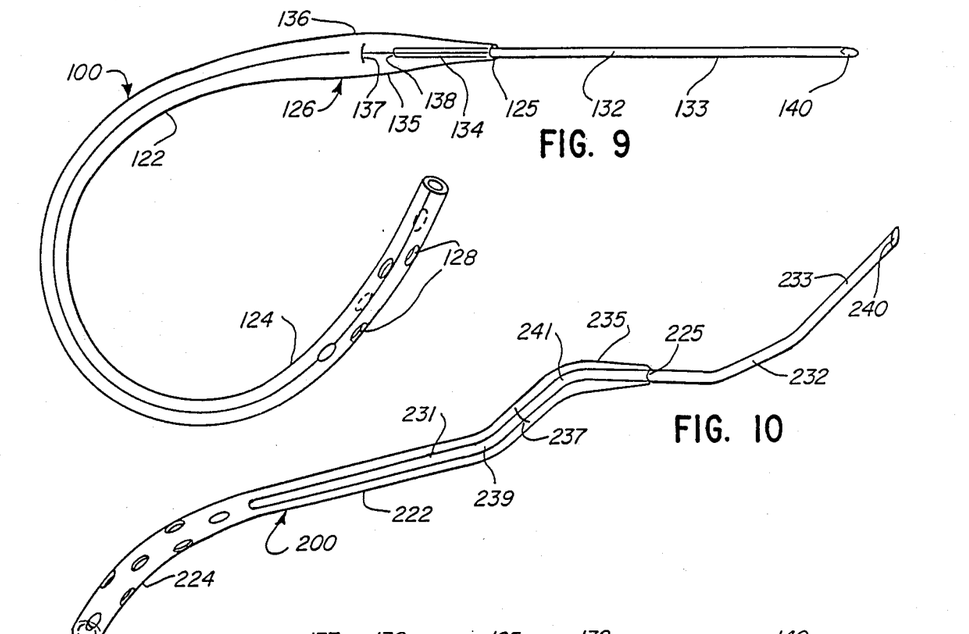
FIG. 9 is an elevational view of a modified form of trocar catheter having an elongated rigid rod.
FIG. 10 is a perspective view of a further modified form of trocar catheter.
Figures 11, 12:
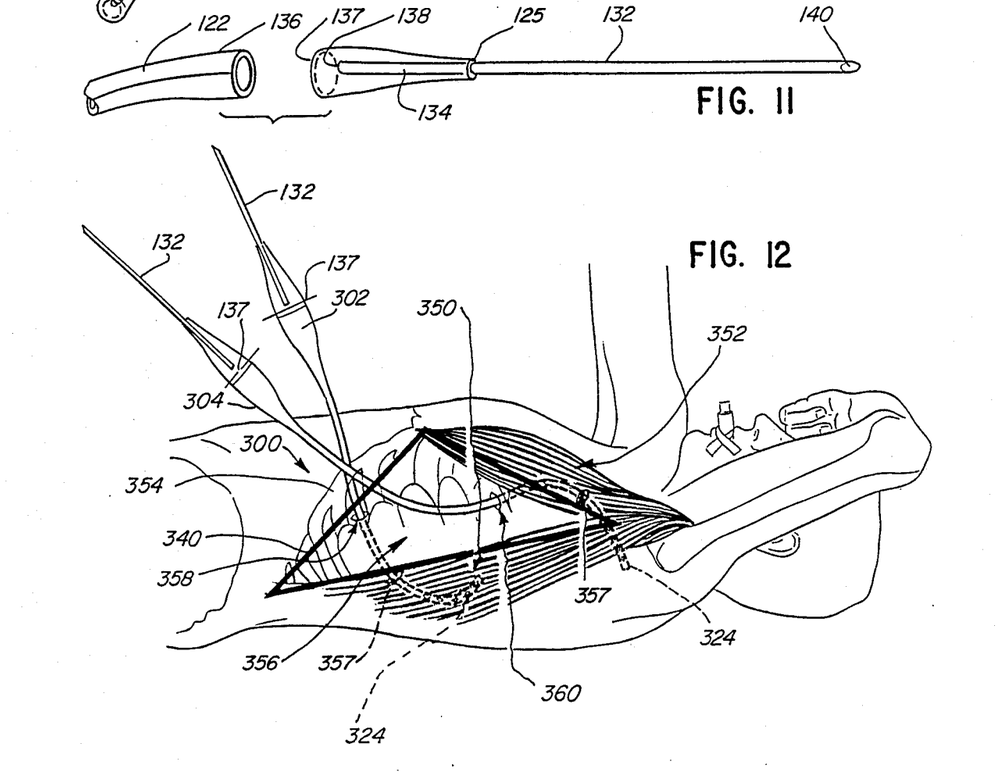
FIG. 11 is a partial elevational view of the form of trocar catheter shown in FIG. 9 only with the tube cropped ready to affix a connector.
FIG. 12 is an elevational view of a patient with two tubes or catheters in place and with the tubes or catheters ready to be cropped and the rigid rod discarded.

FIGS. 9 and 11 show a modified form of MARLIN Tip trocar catheter 100 wherein the tube or catheter 122 is substantially the same as the tube or catheter 22 in FIGS. 2 and 3. The rigid rod 132 extends outward from and inwardly into the proximal end 125 of the tube 122 and is fixed and secured thereto. The rigid rod 132 has an outwardly exposed spike portion 133 which extends several inches from the proximal end 125 of the tube and has a chisel tip 140 at the end thereof. The rod 132 has an inner portion 134 disposed inside the proximal end portion 135 of the tube a short distance and terminates at end 138 short of a high point or mid-portion of the enlarged portion 126 of the tube. The tube 122 has radial openings 128 at the distal end portion 124 and has the enlarged bulbous portion 126 near the proximal end 125 of the tube. A scoring stripe of paint, or other form of designation indicates a "cut-off" line 137 in the vicinity of the high point of the bulbous portion 126. The cut-off line 137 designates where the surgeon should crop the tube 122 after the distal end portion 124 is appropriately placed for suction drainage. Since the enclosed terminal end 138 of the rigid rod 132 is short of the cut-off line 137, when the surgeon crops the tube, he severs only the tube 122 and he does not have to worry about accidentally severing the free end of the rigid rod which free end, if severed, could be left in the operative site.

The rigid rod 132 extends a substantial distance away from the proximal end 125 of the tube. The rod including the extended portion can be shaped so as to facility guiding the chiseled or sharpened end 140 through an area where, due to the small size of the chest cavity of the patient or due to a disease of the patient, the rigid rod must be carefully and skillfully maneuvered so as not to cause additional trauma to the patient. In testing the catheter, the rigid rod has been extended by as much as 7½" from the proximal end of the tube and has been used successfully to locate the proper exit site and then, by applying pressure to the end 134 of the trocar or rod enclosed in the proximal end portion 135 of the tube, forces the chiseled tip 140 to penetrate the chest wall whereupon by pulling the tube through the incision the distal end of the catheter can be place for drainage. The tube 122 is cropped at the cut-off line 137 short of the terminal end 138 of the rigid rod so that the funnel-shaped catheter end can be connected to a connector on an appropriate suction drainage system. The rigid rod 132 and part of the proximal end portion 136 of the tube is disposed of.

FIG. 10 shows another modified form of a MARLIN Tip trocar catheter 200 having a catheter or tube 222 without a bulbous portion in the body of the tube. A bulbous portion could be formed in the tube if desired. A cut-off line 237 is indicated near the proximal end 225 of the tube. If a bulbous portion were formed in the tube, the cut-off 237 would be approximately midway between the ends of the bulbous portion. An elongated rigid rod 232 is fixed or secured in the proximal end portion 235 of the tube with an extended portion or spike 233 of the rod 232 extending outward from the proximal end 225 and an extended portion 231 extending within the tube 222. The outer end or spike 233 of the rod has a chisel point 240 for use in penetrating a chest wall. The material of the rigid rod 232 is such that it is substantially rigid so as to be not only able to transmit forces applied at one end through the rod to the other end but also able to be shaped as desired. For instance, as shown in FIG. 10, the end portion 231 of the rod 232 is given an S shape by excessively doubling the rod and tube over at area 239 and at area 241 several times, each time the rod will partially recoil, retaining some degree of bend, eventually the S shape desired is obtained in the rod and tube. The S shape provides a handle that can be grasped by the surgeon so that the tube and rod will not turn in the hand. Using the handle shape the surgeon can guide the rigid rod through the appropriate open spaces between the organs in the chest cavity to the puncture site. Holding the rod using the handle shape provides the surgeon with the purchase needed to push the chisel tip 240 and rod through the appropriate spot in the chest wall. Once the rod penetrates the chest wall, the rod and catheter are pulled through the new puncture opening until the distal drainage end portion 224 is in the proper position whereupon the tube only is cropped at the cut-off line 237 and the rod and part of the proximal end portion 235 of the tube is pulled apart from the rest of the tube and disposed of. Since the rod 232 is relatively rigid, the surgeon can feel when his scalpel engages the rod whereupon he continues cutting the catheter using the rod as a support or backing. In that way, the rod is not severed.

FIG. 12 is an illustration of a chest area 300 of a patient showing two of the improved MARLIN Tip trocar catheters 302,304 in place to drain two different areas of the chest. The catheters are of the FIGS. 9 and 11 variety such that cropping the tube 122 at the cut-off line 137 and discarding the rigid rod 132 and part o the proximal end portion 135 of the catheter makes it possible to attach the appropriate connector and conduit such that suction can be applied to drain the operative site.

The location of the catheter in the chest cavity so as to deal with real or potential air leaks and with the tip of the catheter at the apex of the thoracic cavity is the same as with prior drainage catheters. One such use is shown and described in the *Craft of Surgery* by Dr. Phillip Cooper, Little Brown & Co., Boston 1964. FIG. 12 is from the book and the text of the book describes the chest wall triangle 340, delineated in FIG. 12 by heavy lines, as an area demarcated by the latissimis dorsi muscle 350, the pectoralis major muscle 352 and the costal arch 354, as the most suitable area for exit of chest tubes, because only one shoulder girdle muscle is traversed, i.e. the Serratus Anterior muscle 356. A point of skin exit 358, 360 of the catheter 302, 304 is selected so that the catheter will not be compressed when the patient is lying in bed and so that the catheter passes through the skin with suitable stability to serve as a point for fixation. Using the improved catheter, the rigid rod 132 can be given some general shaping that will permit maneuvering the rod 132 through the primary surgical incision to a point selected for penetration of the chisel tip 140 through the lining of the chest cavity, the parietal pleura, and to aim for the site on the patient's skin selected for emergence of the catheter. These sites will determine whether the distal end of the catheter lies anteriorly for drainage of air or posteriorly for drainage of liquid, such as blood. Pressure on the handle shaped portion of the rigid rod 132 penetrates the soft tissue of the chest wall (parietal pleura, 357 muscles and their fibrous coverings), but for some patients the protective coverings of the body, i.e. the skin and the subcutaneous fascia, resist penetration and butt-up over the advancing tip of the spike or stiffened proximal end. A scalpel incision through the skin and subcutaneous fascia may be necessary to aid the spike or stiffened proximal end to traverse these structures. Following sound surgical principles, the incision should be slightly longer than the diameter of the catheter employed so that the skin around the catheter at its exit site is not subject to pressure injury. The rigid rod is then pulled through from the outside as the drainage tip 124 is guided to the critical location in the thoracic cavity. The tube 122 is cropped at the cut-off line 137 whereupon the rigid rod is disposed of and a connector and suction source are connected to the funnel-shaped end of the tube.

Heretofore, the catheters were not stiff enough to be self-sustaining as an attempt was made to remotely direct or guide the catheter through the anatomical parts in the chest cavity to the outside-in incision through the chest wall. This was particularly true in small chest cavities such as the chest of a child or where the exposed organs in the chest cavity cannot take the pressure caused by a surgeon's hand, all as was detailed hereinabove. The improved long spike or elongated rigid rod makes it possible to remotely manipulate the rod or spike tip and still have sufficient rigidity to penetrate the chest wall under pressure. Elongating the rigid rod into the catheter makes it possible to shape a handle for controlling the manipulations of the rigid rod. Providing the rigid rod with an enclosed end that is short of the designated cut-off line provides a safety feature that eliminates the possibility that the trocar or rod will have a free end cropped off and fall loosely into the chest cavity.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein.

We claim:

1. A catheter having a distal end portion and a proximal end portion, comprising tubing of flexible material having a passageway extending from a distal end to a proximal end thereof and having at least one radial opening communicating with the passageway at the distal end portion thereof for draining a body cavity, at least a portion of the proximal end portion of the tubing tapering toward the proximal end thereof, a longitudinally facing opening aligned with the passageway in the tubing at the proximal end thereof, and sharpened stiffening means connected with the inside of the passageway at the proximal end portion of the tubing and projecting outwardly from the longitudinally facing opening, said stiffening means extending inwardly beyond said connection with the tubing into the passageway in the tubing, said stiffening means being spaced from the wall of the passageway in the tubing, said spacing extending from the connection of the tubing with the stiffening means to the inner end of the stiffening means, whereby pressure applied to the tubing and underlying stiffening means from inside the body cavity forces the stiffening means and the catheter proximal end portion outwardly through body tissue while simultaneously drawing the catheter distal end portion into the body cavity, whereupon the sharpened stiffening means can be severed from the catheter and the catheter distal end portion positioned in situ.

2. The catheter of claim 1 wherein said stiffening means comprises a rigid rod disposed within and fixed to the inside of the tubing at the proximal end portion of the tubing.

3. The catheter of claim 2 wherein said rigid rod includes a sharpened distal end projecting from the proximal end of the tubing.

4. The catheter of claim 2 wherein said tubing includes an enlarged portion extending axially from the proximal end, said enlarged portion including said portion tapering toward the longitudinally facing opening at the proximal end, said rigid rod being fixed to the tubing within the longitudinally facing opening.

5. The catheter of claim 4 wherein said rigid rod includes a sharpened distal end projecting from the proximal end of the tubing.

6. The catheter of claim 2 wherein said rigid rod is solid.

7. A catheter of claim 1 wherein the stiffening means is comprised of a rigid rod of plastic, metal, wood, bone, ivory or the like.

8. A catheter having a distal end portion and a proximal end portion, comprising a tube of flexible plastic material having at least one radial opening at the distal end portion thereof for draining a body cavity, said tube includes a tapered enlarged portion extending axially of the proximal end thereof, and stiffening means at the proximal end portion of the tube, said stiffening means comprises an integral hardened length of the tube extending only partially into the enlarged portion of the tube, said hardened proximal end portion of the tube terminates at an angle to provide a sharpened proximal end to the stiffening means whereby pressure applied to the hardened length forming the stiffening means from inside the body cavity leads the catheter outwardly through body tissue whereupon the stiffening means can be severed from the catheter and the catheter left in situ.

9. A thoracic catheter having a distal end portion and a proximal end portion comprising tubing of flexible material having a passageway extending from a distal end to a longitudinally facing opening at a proximal end thereof, said tubing having at least one radial opening communicating with the passageway at the distal end portion thereof for draining a body cavity, said tubing having an enlarged portion extending axially of the proximal end and tapering toward the opening at the proximal end, and a rigid rod aligned with and disposed within at least a portion of the length of the passageway in the tubing, said rod being fixed to the inside of the tubing at the proximal end of the catheter, said rod inside said tubing being spaced from the wall of the passageway in the tubing, a second portion of the rigid rod extending from the longitudinally facing opening at the proximal end and having a sharpened outer end, whereby pressure applied to the tubing and rigid rod where the rigid rod is disposed within the tubing from inside the body cavity forces the rigid rod with the catheter proximal end portion outwardly through the body tissue while simultaneously drawing the catheter distal end portion into the body cavity, whereupon the catheter can be severed in the proximal end portion and the rod and proximal end of the catheter can be discarded.

10. The thoracic catheter of claim 9 wherein said rigid rod is solid.

11. The thoracic catheter of claim 9 wherein the rigid rod is metal or the like.

12. A catheter having a distal end portion and a proximal end portion, comprising tubing of flexible material having a passageway extending from a distal end to a proximal end thereof and having at least one radial opening communicating with the passageway at the distal end portion thereof for draining a body cavity, at least a portion of the proximal end portion of the tubing tapering toward the proximal end thereof, a longitudinally facing opening aligned with the passageway in the tubing at the proximal end thereof, and sharpened stiffening means connected with the inside of the passageway at the proximal end portion of the tubing and projecting outwardly from the longitudinally facing opening, said stiffening means extending inwardly beyond said connection with the tubing into the passageway in the tubing, the stiffening means is comprised of a rod of malleable but substantial rigid metal whereby pressure applied to the tubing and underlying stiffening means from inside the body cavity forces the stiffening means and the catheter proximal end portion outwardly through body tissue while simultaneously drawing the catheter distal end portion into the body cavity, whereupon the sharpened stiffening means can be severed from the catheter and the catheter distal end portion positioned in situ.

13. A thoracic catheter having a distal end portion and a proximal end portion comprising tubing of flexible material having a passageway extending from a distal end to a longitudinally facing opening at a proximal end thereof, said tubing having at least one radial opening communicating with the passageway at the distal end portion thereof for draining a body cavity, said tubing having an enlarged portion extending axially of the proximal end and tapering toward the opening at the proximal end, and a rigid rod aligned with and disposed within at least a portion of the length of the passageway in the tubing at the proximal end of the catheter, the rigid rod is a malleable metal, a second portion of the rigid rod extending from the longitudinally facing opening at the proximal end and having a sharpened outer end, whereby pressure applied to the tubing and rigid rod where the rigid rod is disposed within the tubing from inside the body cavity forces the rigid rod with the catheter proximal end portion outwardly through the body tissue while simultaneously drawing the catheter distal end portion into the body cavity, whereupon the catheter can be severed in the proximal end portion and the rod and proximal end of the catheter can be discarded.

14. A thoracic catheter comprising a tube of flexible material having a distal end and a proximal end, at least one radial opening at the distal end thereof for draining a body cavity, an enlarged portion axially spaced from the proximal end and tapering toward both the proximal end and the distal end of the tube, and a rigid rod fixed to the inside of the tube at the proximal end and extending at least in part within the enlarged portion of the tube and being spaced from the wall of at least a portion of the enlarged portion of the tube to provide stiffening means for the portion of the tube adjacent the proximal end, the rigid rod extending several inches beyond the proximal end of the tube and having a sharpened tip at the distal end of the rigid rod.

15. A thoracic catheter comprising a tube of flexible material having a distal end and a proximal end, at least one radial opening at the distal end thereof for draining a body cavity, an enlarged portion axially spaced from the proximal end and tapering toward both the proximal end and the distal end of the tube, and a rigid rod fixed to the inside of the tube at the proximal end to provide stiffening means for the portion of the tube adjacent the proximal end, the rigid rod extending several inches beyond the proximal end of the tube and having a sharpened tip at the distal end of the rigid rod, the rigid rod extending into said tube to a point short of the center of the enlarged portion of the tube.

16. The thoracic catheter as claimed in claim 15 wherein said tube has a cut-off line for severing the tube without intersecting said rod.

17. A thoracic catheter comprising a tube of flexible material having a distal end and a proximal end, at least one radial opening at the distal end thereof for draining a body cavity, an enlarged portion axially spaced from the proximal end and tapering toward both the proximal end and the distal end of the tube, and a rigid rod fixed to the inside of the tube at the proximal end to provide stiffening means for the portion of the tube adjacent the proximal end, the rigid rod extending several inches beyond the proximal end of the tube and having a sharpened tip at the distal end of the rigid rod, the rigid rod extending into and through a substantial portion of the length of the tube, said rigid rod being shapable to desired configurations both inside said tube and outside said tube.

18. A thoracic catheter comprising a tube of flexible material having a distal end and a proximal end, at least one radial opening at the distal end thereof for draining a body cavity, an enlarged portion axially spaced from the proximal end and tapering toward both the proximal end and the distal end of the tube, and a rigid rod fixed to the inside of the tube at the proximal end to provide stiffening means for the portion of the tube adjacent the proximal end, the rigid rod extending several inches beyond the proximal end of the tube and having a sharpened tip at the distal end of the rigid rod, said rod inside said tube being formed into a flat S shape to provide a handle for controlling the direction the sharpened distal tip is following.

19. A thoracic catheter comprising a tube of flexible material having a distal end portion and a proximal end portion, at least one radial opening at the distal end portion thereof for draining a body cavity, an enlarged portion axially spaced from the proximal end portion and tapering toward both the proximal end portion and the distal end portion of the tube, a rigid rod disposed within and fixed to the inside of the tube at the proximal end portion to stiffen the proximal end portion of the tube, the rigid rod having a sharpened distal end, the rigid rod extending several inches beyond the proximal end portion of the tube and extending axially from the distal end portion a substantial length on the inside of the tube, the rigid rod inside the tube being shapable into a handle shape along with the tube so as to provide the surgeon with a positive grip on the tube and rod thereby preventing turning of the tube and rod as it is manipulated into place.

20. A thoracic catheter having a distal end portion and a proximal end portion comprising tubing of flexible material having a passageway extending from a distal end to a proximal end thereof and having at least one radial opening communicating with the passageway in the portion of the tube adjacent the distal end thereof for draining a body cavity, and a rigid rod disposed within and fixed to the inside of the tubing at the portion of the tubing adjacent the proximal end to provide a stiffening means for the tubing overlapping the rigid rod, a cut-off line in the tubing beyond the proximal end of the rigid rod, the rigid rod extending several inches beyond the proximal end of the tubing and having a sharpened outer end, whereby pressure applied to the tubing and rigid rod from inside the body cavity first forces the rigid rod and then the rigid rod and catheter proximal end portion outwardly through body tissue while simultaneously drawing the catheter distal end portion into the body cavity, whereupon the catheter distal end portion is positioned in situ and the tubing can be severed at the cut-off line short of the end of the rod to assure that the end of the rod is not severed and lost in the body cavity.

21. A thoracic catheter comprising a flexible tubing having a distal end and a distal end portion, and a proximal end and a proximal end portion, openings formed in the distal end portion thereof for draining a body cavity, and a rigid rod disposed within at least a portion of the length of the tubing and fixed to the inside of the tubing at the proximal end thereof to provide stiffening means for the portion of the tubing overlapping the rigid rod, said rigid rod extending several inches beyond the proximal end of the catheter and having a sharpened distal end, said rigid rod being shapable so as to be manipulable in the chest cavity from a remote site so as to neither disturb nor apply pressure to exposed organs in the chest cavity, whereby pressure applied to the overlapping tubing and rigid rod forces the rigid rod first and then the rigid rod and the catheter proximal end portion outwardly through the body tissue while simultaneously drawing the catheter distal end portion into the body cavity, whereupon the catheter proximal end portion can be severed and the rigid rod and proximal end of the catheter can be disposed of.

22. A thoracic catheter comprising tubing of flexible material having a distal end portion and a proximal end portion, a passageway in the tubing extending from at least one radial opening in the distal end portion to a longitudinally facing opening at the proximal end portion thereof, a rigid rod disposed within a portion of the length of the passageway and fixed to the inside of the tubing adjacent the longitudinally facing opening at the proximal end portion to stiffen the portion of the tubing overlapping the rigid rod, the rigid rod extending beyond the proximal end portion of the tubing and having a sharpened distal end, the rigid rod inside the tubing being shapable into a handle shape along with the tube so as to provide the surgeon with a positive grip on the overlapping tubing and rod thereby preventing turning of the tubing and rod as it is manipulated into place.

23. A thoracic catheter comprising tubing of flexible material having a distal end portion and a proximal end portion, at least one radial opening at the distal end portion thereof for draining a body cavity, the proximal end portion of the tubing tapering toward the proximal end of the tubing, and a rigid rod loosely positioned within a portion of the length of the tubing and fixed to the inside of the tubing at the proximal end of the tubing to provide stiffening means for the portion of the tubing overlapping the rigid rod at least adjacent the proximal end portion thereof, the rigid rod extending beyond the proximal end of the tubing and having a sharpened distal tip at the distal end thereof.

24. The catheter as claimed in claim 23 wherein said tubing has a cut-off line for severing the tubing without intersecting said rod.

25. The thoracic catheter as claimed in claim 23 wherein said rigid rod extends into and through a substantial portion of the length of the tube, said rigid rod being shapable to desired configurations both inside said tube and outside said tube.

26. A thoracic catheter having a distal end portion and a proximal end portion comprising tubing of flexible material having a passageway extending from a distal end to a proximal end thereof and having at least one radial opening communicating with the passageway in the portion of the tube adjacent the distal end thereof for draining a body cavity, and a rigid rod having a portion loosely disposed within the proximal end portion of the tubing and being fixed to the inside of the tubing at the portion of the tubing adjacent the proximal end to provide a stiffening means for the portion of the tubing that overlaps the rigid rod, the rigid rod having another portion extending beyond the proximal end of the tubing and having a sharpened outer end, whereby pressure applied to the tubing and rigid rod from inside the body cavity first forces the rigid rod and then the rigid rod and catheter proximal end portion outwardly through body tissue while simultaneously drawing the catheter distal end portion into the body cavity, whereupon the catheter distal end portion is positioned in situ and the tubing can be severed short of the end of the rod to assure that the end of the rod is not severed and lost in the body cavity.

27. A thoracic catheter comprising a flexible tubing having a distal end and a distal end portion, and a proximal end portion, openings formed in the distal end portion thereof for draining a body cavity, and a rigid rod disposed within at least a portion of the length of the tubing and fixed to the inside of the tubing at the proximal end thereof to provide stiffening means for the portion of the tubing overlapping the rigid rod, said rigid rod loosely fitting in the overlapping portion of the tubing and extending beyond the proximal end of the tubing, said rigid rod having a sharpened outer end and being shaped so as to be manipulable in the chest cavity from a remote site so as to neither disturb nor apply pressure to exposed organs in the chest cavity, whereby pressure applied to the overlapping tubing and rigid rod forces the rigid rod first and then the rigid rod and the catheter proximal end portion outwardly through the body tissue while simultaneously drawing the catheter distal end portion into the body cavity, whereupon the catheter proximal end portion can be severed and the rigid rod and proximal end of the catheter can be disposed of.

28. A thoracic catheter comprising tubing of flexible material having a distal end portion and a proximal end portion, a passageway in the tubing extending from at least one radial opening in the distal end portion to a longitudinally facing opening in the proximal end portion thereof, a rigid rod loosely disposed within a portion of the length of passageway and fixed to the inside of the tubing adjacent the longitudinally facing opening at the proximal end portion to stiffen the portion of the tubing overlapping the rigid rod, the rigid rod extending beyond the proximal end portion of the tubing and having a sharpened distal end, the rigid rod loosely disposed in the passageway in the tubing being shaped into a handle shape along with the tubing so as to provide the surgeon with a positive grip on the overlapping tubing and rod thereby preventing turning of the tubing and rod as it is manipulated into place.

* * * * *

UNITED STATES PATENT AND TRADEMARK OFFICE
CERTIFICATE OF CORRECTION

PATENT NO. : 4,883,474

DATED : November 28, 1989

INVENTOR(S) : David S. Sheridan and Ralph D. Alley

It is certified that error appears in the above-identified patent and that said Letters Patent is hereby corrected as shown below:

Column 4, line 24, after "For" insert --instance--.

Column 7, line 18, change the last word "facility" to --facilitate--;
line 31, after "be", change "place" to --placed--;
line 37, cancel the first word "is" and insert in lieu thereof --are--.

Column 8, line 7, cancel the first word "is" and insert in lieu thereof --are--;
line 17, after "part" cancel "o" and insert in lieu thereof --of--

Column 14, line 22 (Claim 27), after "distal end portion," insert -- and a proximal end--

Signed and Sealed this

Sixth Day of August, 1991

*Attest:*

HARRY F. MANBECK, JR.

*Attesting Officer*   *Commissioner of Patents and Trademarks*